United States Patent
Wolfer

[11] Patent Number: 5,813,979
[45] Date of Patent: Sep. 29, 1998

[54] EKG DEVICE HAVING INDIVIDUALLY STORABLE ELETRODE LEADS

[76] Inventor: Donna A. Wolfer, 4455 S.W. 68 Ave., Davie, Fla. 33314

[21] Appl. No.: 853,197

[22] Filed: May 9, 1997

[51] Int. Cl.$^6$ .................................................. A61B 5/02
[52] U.S. Cl. ............................................. 600/393; 600/508
[58] Field of Search ................................. 600/382, 384, 600/393, 508, 509, 522, 520

[56] References Cited

U.S. PATENT DOCUMENTS

| | | | |
|---|---|---|---|
| 3,821,496 | 6/1974 | Malone | 600/508 |
| 4,280,507 | 7/1981 | Rosenberg . | |
| 4,353,372 | 10/1982 | Ayer . | |
| 4,573,474 | 3/1986 | Scibetta . | |
| 5,033,474 | 7/1991 | Varelis et al. | 600/509 |
| 5,074,863 | 12/1991 | Dines | 606/41 |
| 5,184,620 | 2/1993 | Cudahy et al. . | |
| 5,341,812 | 8/1994 | Allaire et al. . | |
| 5,546,950 | 8/1996 | Schoeckert et al. . | |

Primary Examiner—William E. Kamm
Assistant Examiner—George R. Evanisko
Attorney, Agent, or Firm—Malin, Haley, DiMaggio & Crosby, PA

[57] ABSTRACT

A portable EKG machine having a plurality of individually storable electrode leads, each of which may be selectively moved from a retracted position wherein the electrode lead is stored within a storage enclosure, to an extended position wherein the electrode lead is drawn from the storage enclosure. The EKG machine of the present invention includes a monitor, a storage enclosure and a plurality of conducting leads each terminating in an electrode. In a preferred embodiment, the storage enclosure includes a plurality of retractable and extendable leads mounted on individual rotatable spools enclosed therein. Each electrode and lead may be individually selectively extended by an EKG technician by grasping and separating an electrode from the storage enclosure thereby unwinding the lead from its storage spool to an extended position, whereafter the electrode may be conductively attached to the patient's body. Upon removal of one or more electrodes from the patient's body, the spools provide for automatic retraction of each individual lead to its stored position thereby eliminating entanglement problems associated with dangling leads.

8 Claims, 4 Drawing Sheets

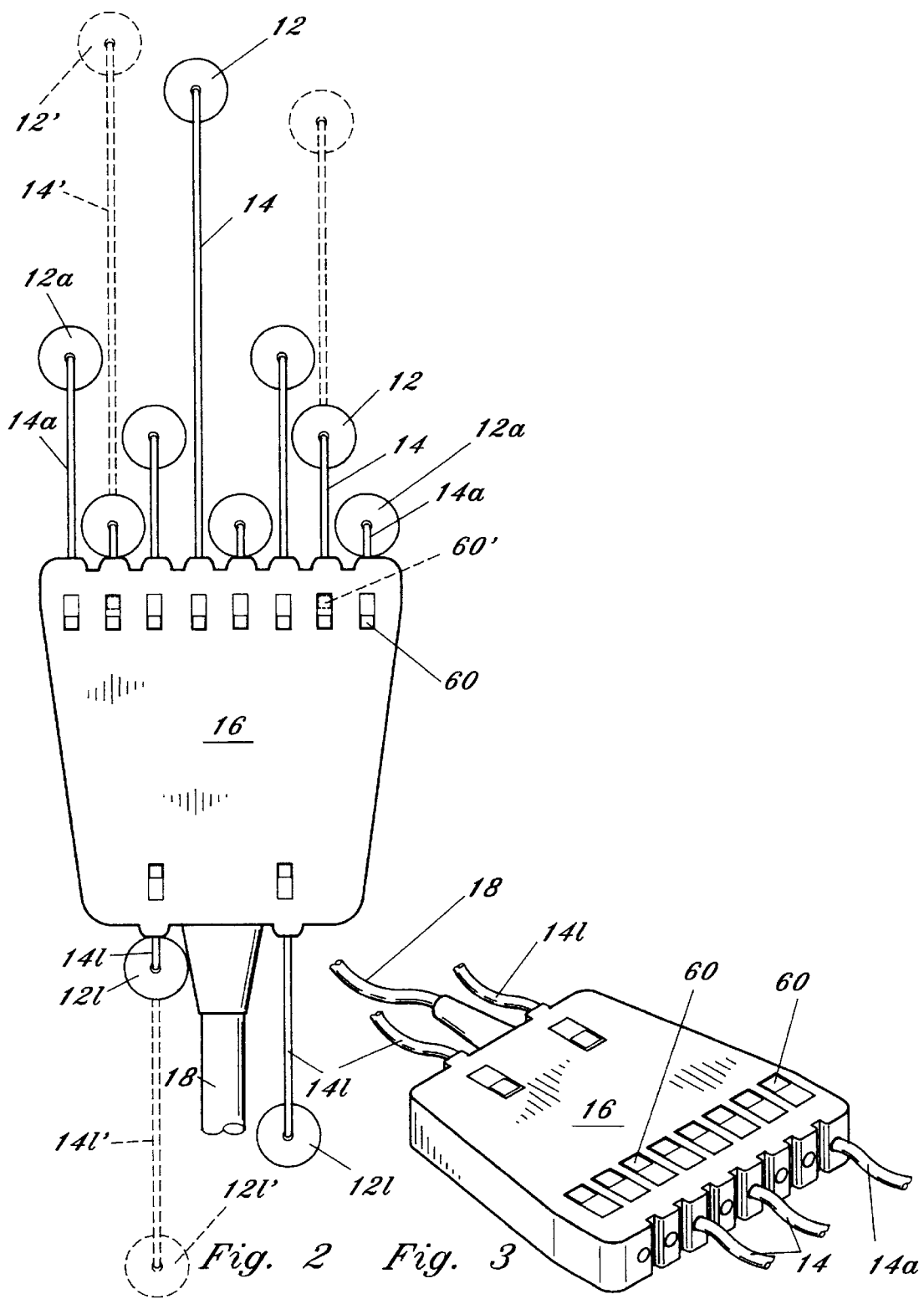

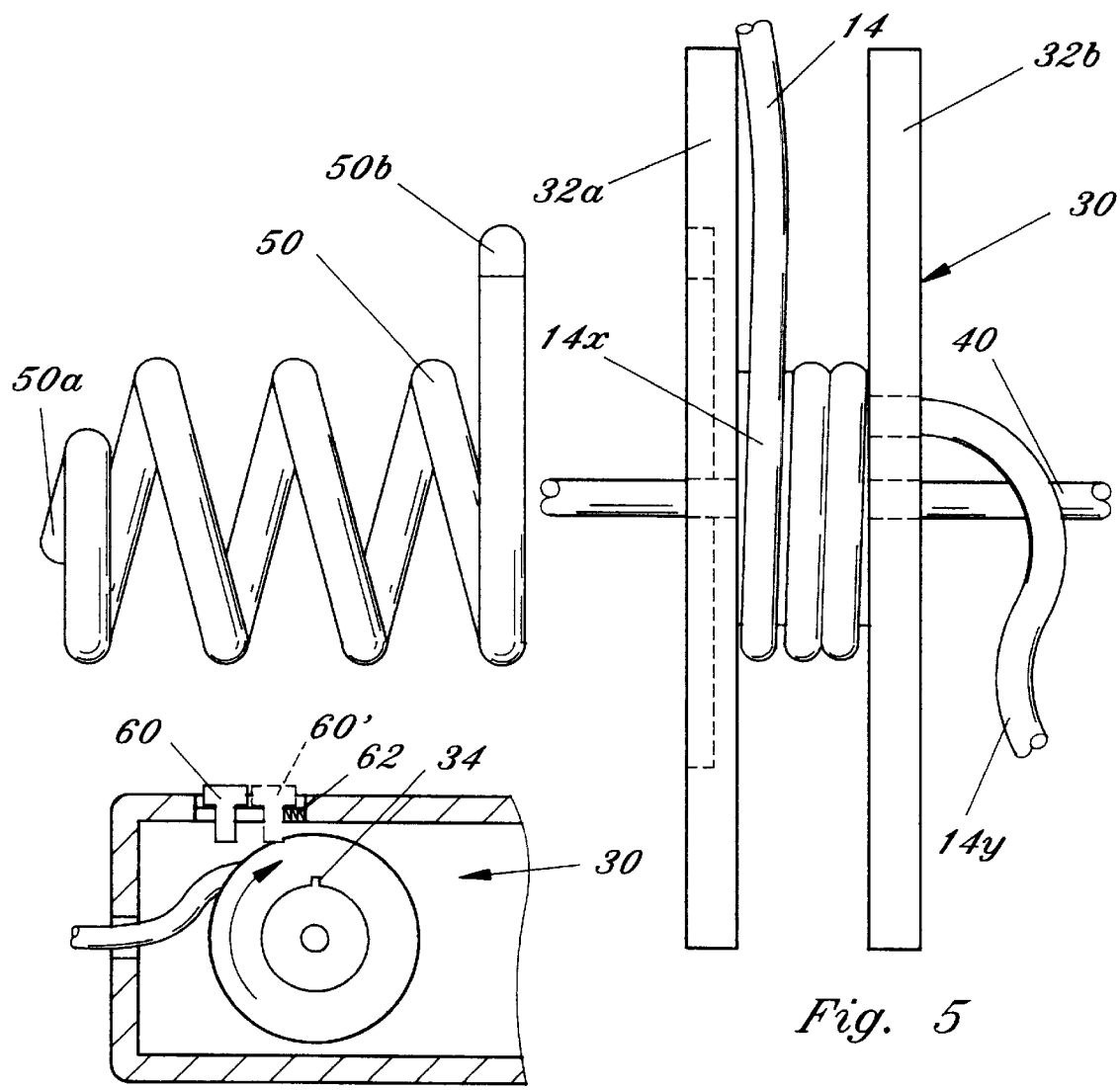
Fig. 5
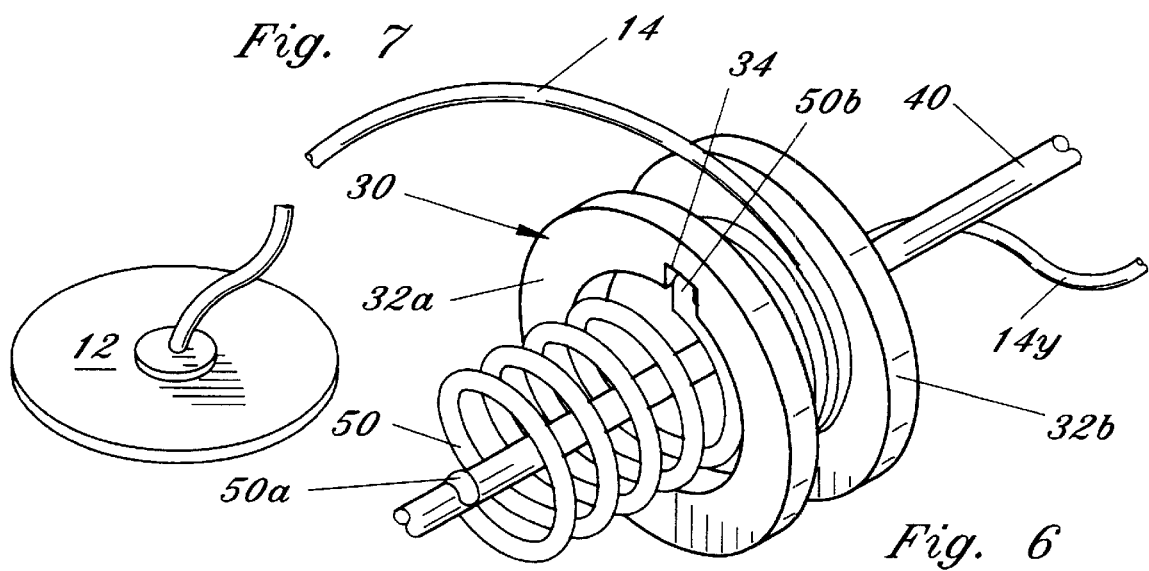
Fig. 7
Fig. 6

EKG DEVICE HAVING INDIVIDUALLY STORABLE ELETRODE LEADS

BACKGROUND OF THE INVENTION

1. Field of the Invention

The present invention relates to electrocardiograph heart monitoring devices, commonly referred to as EKG machines, and more particularly to an electrocardiograph device having individually storable conductors for expeditiously facilitating the manual administration, storage, and dispensing of individual electrode leads to a patient, especially in emergency situations.

2. Description of the Background Art

An electrocardiogram is a graphic recording of the electrical manifestations of heart activity as obtained from electrode sensors placed on a patient's skin. An electrocardiograph is an instrument used to obtain an electrocardiogram. An electrocardiograph machine (hereinafter "EKG machine") may include as many as electrically conductive wires (hereinafter "leads") each having a terminal end electrically connected to an electrode. To sense heart activity a plurality of electrodes are placed in electrical and physical contact with selected points on the patients skin. Typically, a plurality of leads are grouped or bundled together at a cable harness which has one or more connectors which can be plugged directly into an EKG monitor. Prior art EKG harnesses commonly comprise a plurality of electrodes each existing on the distal end of an elongated conducting lead.

A common problem present with the operation of EKG machines involves difficulty in setup and operation. In particular, the EKG technician, paramedic or nurse responsible for coupling the EKG electrodes to a patient's body often experiences problems with entanglement of the EKG leads. Moreover, entanglement of the EKG leads often produces further undesirable consequences such as tangle induced stress on an attached and functioning electrode which may cause the electrode to detach from the patient's body. Furthermore, since emergency paramedics often have minimal time to establish the instantaneous medical condition of accident or heart attack victims, time literally becomes a life or death variable. When an emergency paramedic first arrives at a victim's side, the first procedure is often to establish the cardiac condition of the patient. However, conventional portable EKG monitors have numerous unstored leads that easily get tangled with each other during an emergency application. The present invention is especially suited for producing an EKG reading in an emergency situation where time is critical. According to the present invention, each electrode lead remains out of the way until the paramedic manually grasps the lead and attaches the electrode to the patient's body.

Another problem experienced with the use of multiple EKG leads during an EKG procedure that must be interrupted by medical necessity is that the electrodes must often be intentionally detached from the patient's body in order to administer emergency treatment. For example, it may become necessary to quickly remove the chest mounted electrodes of the EKG monitor, when the patient is experiencing certain heart abnormalities, for the purpose of defibrillation or, for massaging the heart, or for administering drugs. Accordingly, electrodes that have been detached from the patient's body often dangle by their respective leads in an unsecured fashion thereby presenting a further entanglement potential.

The following patents disclose various attempts to overcome the above-referenced problems experienced with the use EKG devices.

U.S. Pat. No. 4,280,507 issued to Rosenberg discloses a harness for connecting the inputs of an EKG machine to electors attached to the body of the patient. However, Rosenberg is directed to providing distributed resistance sufficient to protect the EKG machine from defibrillation pulses, and does not adequately remedy the problem experienced with entanglement of the leads.

U.S. Pat. No. 4,353,372 issued to Ayer discloses a unitary medical cable set designed for electrical connection for plurality of body locations providing a completely metal free disposable body electrode in the form of a cable which resists entanglement. Ayer attempts to minimize the entanglement problem by merging individual branch leads into a common trunk.

U.S. Pat. No. 4,573,474 issued to Scibetta discloses a complex cable harness for an electrocardiogram device having spring biased laterally extending arms, side arms perpendicularly attached to the lateral arms, a swivel joint mounted on the top of the central unit, a bottom attached to the swivel joint; and plurality of EKG electrodes attached to the bottom, lateral arms, and side arms to monitor the electrical activity of the heart.

U.S. Pat. No. 5,033,474 issued to Varelis, et al. discloses a cable storage means for use with an EKG machine. Varelis discloses a plurality of spools around which cables can be wound for preventing tangling. However, having to wind the EKG leads about a spool is time consuming and inefficient.

U.S. Pat. No. 5,184,620 issued to Cudahy, et al. discloses a multiple electrode pad assembly for monitoring electrical impulses from a patients heart. Cudahy addresses the entanglement problem by fixing each of the electrodes on to a integral pad; however, such placement greatly limits the ability of the physician in attaching the electrodes to the patient's body at desirable locations.

U.S. Pat. No. 5,341,812 issued to Allaire, et al. discloses an electrocardiogram system having a single electrocardiograph cable used to interconnect a plurality of lead wires extending from a plurality of associated medical electrodes. However, Allaire is directed to an adapter arrangement for an EKG monitor which limits the number of different EKG cables needed for use with a wide variety of EKG monitors and ensures proper operation of the monitors, and is not directed to the problem of entanglement.

U.S. Pat. No. 5,546,950 issued to Schoeckert, et al. discloses an EKG patient lead cable apparatus having a plurality of connecting wires with connectors for electrodes joined together for varying portions of their length to form a flat common portion of cable.

The prior art does not disclose an EKG harness which provides individually retractable and extendable leads and electrodes for eliminating the entanglement problems associated with the electrode leads. The present invention is directed toward overcoming this, and other problems and disadvantages present in the background art.

SUMMARY OF THE INVENTION

A portable EKG machine having a plurality of individually storable electrode leads, each of which may be individually, selectively moved from a retracted position wherein each electrode lead is stored within a storage enclosure, to an extended position wherein the electrode lead is drawn from the storage enclosure. The EKG machine of the present invention includes a monitor, a storage enclosure and a plurality of conducting leads, each lead terminating in an electrode.

In a preferred embodiment, the storage enclosure includes a plurality of retractable and extendable leads mounted on individual rotatable spools enclosed therein. Accordingly, each electrode lead is disposed in a wound configuration about an individual spool in a normally retracted position such that the electrode existing at the terminal end of the lead functions as a stop when the lead is fully retracted and assumes a position substantially adjacent to the storage enclosure, whereby the storage enclosure functions to contain a plurality of individually rotatable spools, as well as the leads when retracted. Each spool is rotationally biased in a rotational direction corresponding to the retracted position. Thus, when the leads are retracted they do not dangle or hang freely, and thus the problems experienced with lead wire tangling have been eliminated.

Each lead may be individually and selectively extended manually by the EKG technician by grasping and separating an electrode from the enclosure thereby unwinding the lead from its storage spool such that the electrode is pulled away from the enclosure to an extended position, whereafter the electrode may be conductively attached to the patient's skin for detecting electrical signals relating to the activity of the patient's heart. Should the EKG technician have to remove one or more electrodes from the patient's body, each individually rotatable, spring biased spool provides for automatic retraction of an individual lead into the enclosure thereby eliminating entanglement problems associated with freely dangling leads. The preferred embodiment has selective spool stops for rotational anchoring of individual spools such that one or more electrode leads may be selectively maintained in an extended position.

While the preferred embodiment employs spring biased rotational spools to retract and store electrode leads, alternate structures may be used to accomplish the desired results. For example, gravitational retraction of leads, or the use of elastic members or spring members attached to each lead to facilitate biased self retraction.

Accordingly, it is an object of the present invention to facilitate the administration of individually stored EKG electrodes in emergency situations.

It is a further object of the present invention to provide an improved EKG machine which eliminates entanglement of electrode leads.

Yet another object of the present invention is to provide an EKG machine having a plurality of individually retractable electrodes.

Still another object of the present invention is to provide an EKG machine having individually retractable electrodes with each lead stored on a single individually rotatable spool when in a retracted configuration.

An additional object of the present invention is to provide a simple and reliable EKG machine having a storage enclosure for electrode leads which allows for selective use of individual electrodes while maintaining those electrodes not in use in retracted, yet readily accessible storage.

It is a further object of the present invention to provide an EKG machine having a storage enclosure containing internal spools for storing electrode leads in a wound configuration when retracted.

Yet another object of the present invention is to provide an EKG machine having a plurality of electrodes maintained in a retracted position until drawn to an extended position by a user.

In accordance with these and other objects which will become apparent hereinafter, the instant invention will now be described with particular reference to the accompanying drawings.

BRIEF DESCRIPTION OF THE DRAWINGS

FIG. 2 is a top plan view of the present invention;

FIG. 3 is a front perspective view of the present invention;

FIG. 5 is an exploded partial detail of an embodiment of a lead storing spool of the present invention;

FIG. 6 is a partial side perspective view of a lead storing spool of the present invention;

FIG. 7 is a partial side sectional view detailing an embodiment of a spool locking mechanism.

DESCRIPTION OF THE PREFERRED EMBODIMENTS

Figure 1:
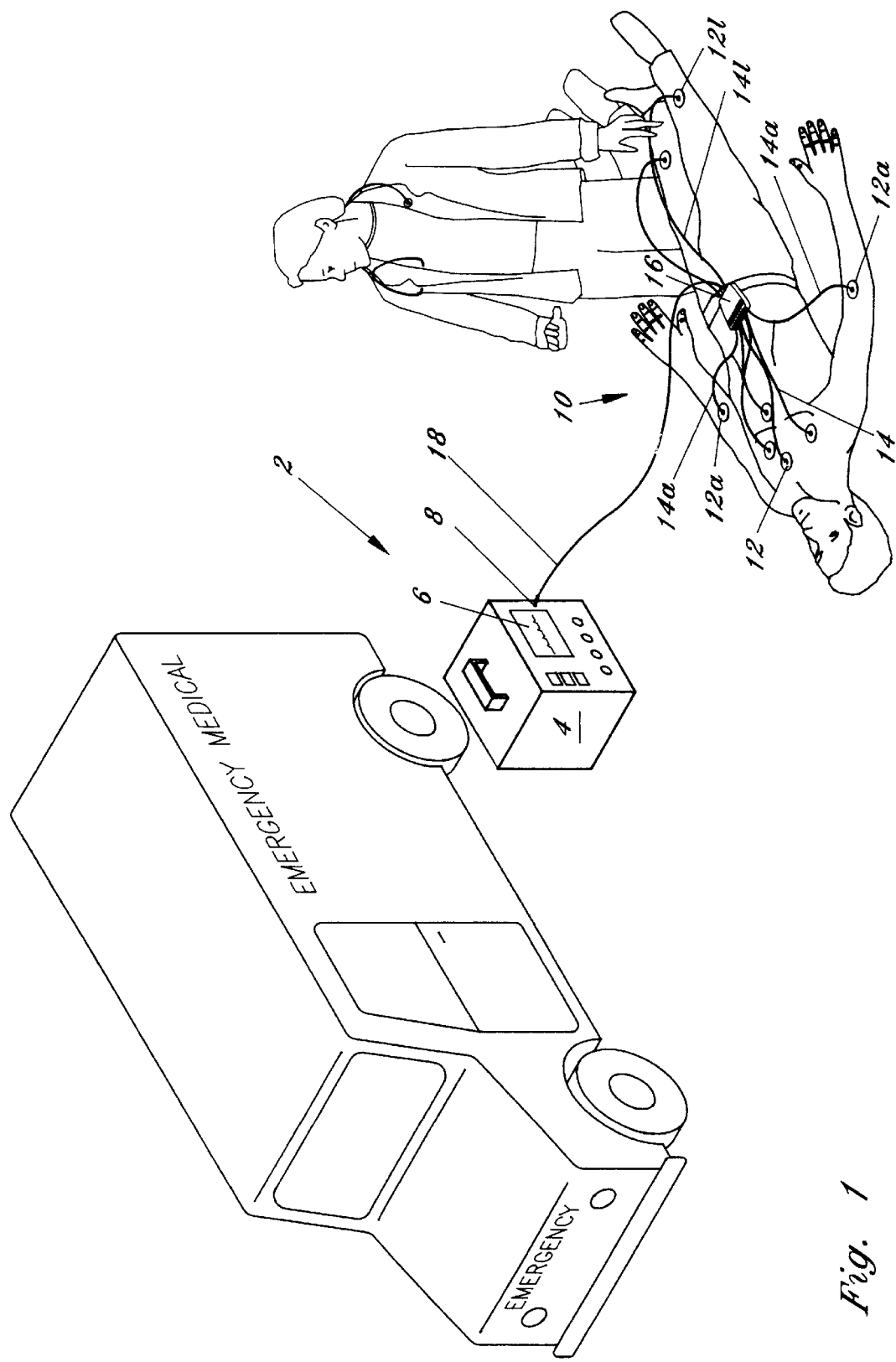
FIG. 1 is a perspective view illustrating use of an EKG machine according to the present invention by an emergency technician.

In FIG. 1, there is depicted a preferred embodiment of the improved EKG machine of present invention, referenced generally as 2. The improved EKG machine includes a monitor 4 having a display 6 and an input port 8. An EKG electrode assembly, generally referenced as 10, and including electrodes 12, electrode leads 14, storage housing 16 and cable 18, is electrically connected to the EKG machine by connecting inserting cable 18 into port 8. Electrodes 12 function as sensors for electrically detecting signals generated by the activity of a person's heart when the electrodes are adhesively secured to the person's skin. The signals detected by electrodes 12 are transmitted to the EKG machine via leads 14 and thereafter via cable 18, whereby the EKG monitor 4 transforms the signals detected by the electrodes into a corresponding pattern on display 6. The pattern viewed on display 6 provides the EKG technician with valuable information about the heart activity of the patient.

As best depicted in FIGS. 2 and 3, electrode assembly 10 includes a plurality of EKG electrodes 12, each electrode is conductively connected to the distal end of an electrode lead 14. Electrodes 12 may be fabricated from any suitable conducting material, and in the preferred embodiment are fabricated from surgical grade stainless steel. Additionally, the electrodes must be relatively chemically inert with respect to any conducting gel used when adhesively securing the electrode to the patient's body.

Leads 14 each comprise an insulated electrical conductor and each lead is routed through storage enclosure 16 for electrical connection to an EKG monitor 4 via connecting cable 18. In the preferred embodiment each lead 14 comprises a flexible insulated electrical conductor, however, any suitable electrically conducting material is within the scope of the invention.

Electrodes 12 and leads 14 function to sense and transmit electrical signals relating to heart activity to EKG monitor 4. EKG monitor 4 includes circuitry for transforming the electrical signals detected by electrodes 12 into an observable output which may be displayed to the EKG technician or paramedic on display 6. Electrodes 12 are used to detect heart activity by adhesively securing a plurality of electrodes to the patient's skin thereby placing the electrodes in electrical communication with the patient's heart. As depicted in FIG. 1, certain electrodes and leads are attached to the patient's arms (referenced as 12a and 14a), while other electrodes and leads are attached to the patient's legs (referenced as 12l and 14l), while the remaining electrodes and leads are attached to the patient's torso (referenced as 12 and 14).

Figure 4:
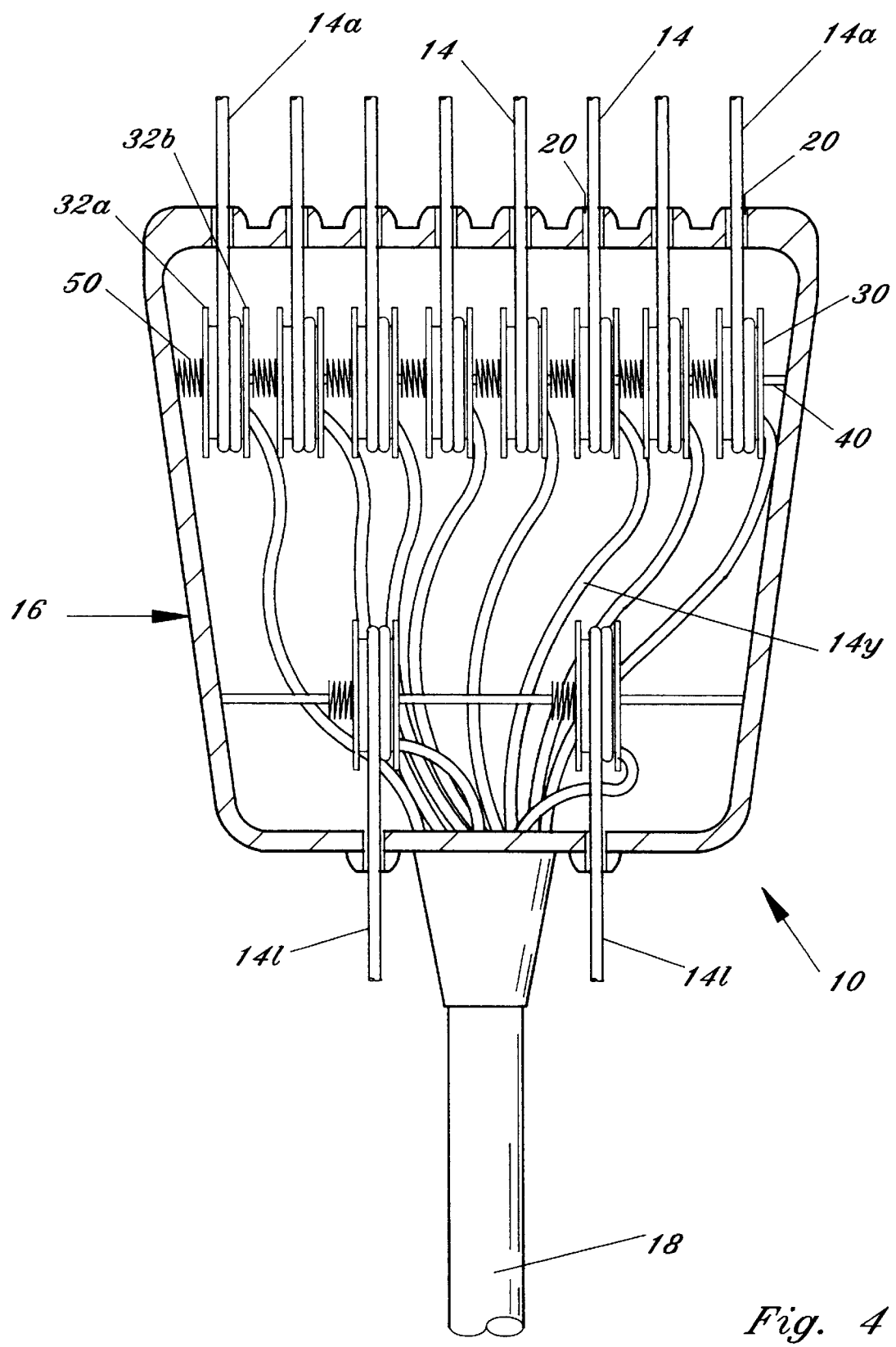
FIG. 4 is a top plan view as depicted in FIG. 2 with the top cut away.

As depicted in FIG. 4, storage enclosure 16 defines an interior volume and a plurality of lead accommodating apertures 20. Each lead 14 passes through a housing aperture 20 to the housing interior volume. Enclosure 16 may be fabricated from thermoplastic or any other suitable material and may be fabricated using injection molding techniques. In addition, enclosure 16 may be a separate component as depicted in FIG. 1, or it may be an integral part of monitor 4.

In the preferred embodiment, enclosure 16 includes a plurality of cylindrical spools 30. Spools 30 each comprise a cylindrical body having a pair of opposing rims 32a and 32b and a central hub having an axial opening therethrough. Each spool is rotatably supported by an axle 40, having a portion thereof disposed within the central hub axial opening, and axle 40 has end portions supportably affixed to housing 16. As is now apparent, spools 30 are each independently rotatable while supported on axle 40. It should be noted however, that any structure which provides for independent storage and individual selective extension and retraction of leads 14 falls within the scope of the invention.

Each spool 30 is rotatably biased in a rotational direction which results in the lead 14, associated with a particular spool, being wound about the spool. In the preferred embodiment spring biasing is accomplished by a plurality of helical springs 50. As depicted in FIGS. 4, 5, and 6, a helical spring 50 is individually associated with each spool 30, for the purpose of providing rotational bias to a spool independent of the remaining spools. In the preferred embodiment, each helical spring has a first end 50a attached to a fixed mount, such as axle 40, and a second end 50b attached to a spool 40. As best seen in FIG. 6, attachment of the second spring end 50b to the spool may be accomplished by insertion of the spring end 50b within a notch 34 formed on one of the spool rims 32a or 32b. The spring stores potential energy as the lead is drawn from the storage enclosure thereby biasing the spool. It should be noted, however, that the present invention should not be narrowly construed to the specific lead retracting structure disclosed herein, and that any rotational mechanical potential energy storage device for returning each electrode lead to a retracted position within enclosure 16 is within the scope of the invention.

As further depicted in FIG. 6, each lead includes a portion thereof, generally referenced as 14x, wound about a spool hub and a further portion thereof, generally referenced as 14y, electrically interfacing with connecting cable 18, whereby electrical signals may be transmitted from an electrode 12 directly to the EKG monitor 4. It should be noted that the present invention is directed to any EKG monitor and electrode combination regardless of the configuration leads and/or connecting cable 18. As is now apparent, leads 14, spools 30, axle 40, and springs 50, cooperate within storage enclosure 16 to provide individually retractable and extendable leads which are both selectively and individually extendable and spring biased to a retracted storage position.

The improved function of the assembly 10 of the present invention is best illustrated in FIG. 2, wherein there is shown a plurality of electrodes 12 and cables 14, in varying extended and retracted positions. As depicted in phantom, electrode 12' and 14' are in an extended position. When in the retracted position, electrode 12 is positioned substantially adjacent to storage enclosure 16 and may be prevented from further retraction since electrode 12 is much larger in size than the size of enclosure opening 20 and thus functions as a retraction stop. In the retracted position, a portion of lead 14, referenced as 14x, is wound about its respective spool 30, and its respective spool spring 50 is substantially relaxed. When in the extended position, electrode 12 is positioned in spaced relation with enclosure 16 such that a portion of lead 14 is fed from its respective spool 30 through one of housing apertures 20. As each cable is manually drawn from its respective spool, the spool is caused to rotate about axle 40 thereby loading its respective spring with potential energy thereby placing the spring under tension. When loaded with potential energy, the spring 50 provides a retracting bias to its respective spool for facilitating selective and automatic retraction of a lead 14 to a retracted position. Therefore each lead 14, 14a and 141 is selectively extendable and retractable. Note that in the preferred embodiment, leads 14 and 14a extend out one side of enclosure 16, while leads 141 extend out of the opposite side of enclosure 16 such that there is no need to have any lead double back across the enclosure.

As depicted in FIG. 7, the preferred embodiment further contemplates a mechanical stop 60 for selective rotational locking of an individual spool 30 once the spool's respective electrode and lead have been drawn by the user to the desired extended position. In the preferred embodiment, storage enclosure 16 includes a plurality of spool locking buttons 60 each of which is positioned in alignment with an underlying spool. Each spool locking button is movable from a first position, referenced as 60, wherein the spool is not engaged and is thus free to rotate, to a second position, referenced as 60', wherein the spool is engaged, and thus not free to rotate. While rotational locking of the spools is accomplished by buttons 60 in the preferred embodiment, any mechanical spool locking stop or friction device or rachet mechanism is within the scope of the present invention. Furthermore, it is desirable that each locking button be independently biased to the second position 60'. In the preferred embodiment the buttons may be biased by helical spring 62; however, any biasing structure is considered within the scope of the invention. Thus, when any lead is drawn to an extended position, spring 62 automatically locks the respective spool 30 thereby allowing the EKG technician to efficiently affix an electrode to a desired location on the patient's skin.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An EKG machine having a plurality of individually storable electrode leads each terminating in an electrode, said EKG machine comprising:

a monitor having means for generating output;

a plurality of electrodes for sensing electrical activity generated by a person's heart;

said of said plurality of electrodes individually electrically connected to said monitor by a corresponding plurality of elongated electrically conducting flexible leads; and an enclosure, said enclosure including means for storing each of said plurality of electrode leads, each of said plurality of leads being selectively and individually movable from a retracted position wherein the lead is substantially stored within said enclosure, to an extended position wherein the lead is substantially drawn from said enclosure;

said enclosure having opposing first and second ends, each of said ends having a plurality of leads dispensed therefrom, whereby said enclosure may be disposed proximal to a patient's torso and leads may be dispensed toward the patient's upper torso from said first end, and additional leads may be dispensed toward the patient's lower torso and legs.

2. An EKG machine according to claim 1, wherein said means for storing further includes means for individually biasing each of said electrode leads to said retracted position within said enclosure.

3. An EKG machine according to claim 2, wherein said means for storing includes:

a plurality of rotatable spools supported by said enclosure, each of said spools having a portion of one of said electrode leads at least partially wound thereon;

each of said rotatable spools being rotationally biased in a rotational direction, corresponding to said retracted position, by said means for individually biasing, whereby said leads are biased to a retracted position wound about one of said plurality of rotatable spools.

4. An EKG machine according to claim 3, further including means for selective and individual rotational locking of each of said rotatable spools.

5. An assembly of sensors for use with an EKG machine for detecting and transmitting signals relating to heart activity, said assembly of sensors comprising:

a plurality of electrodes, each electrode electrically connected to a conducting lead, each lead electrically connected to a cable terminating in at least one connector for electrical connection to an EKG monitor;

a storage enclosure having means for retractable storage of each of said leads, said means for retractable storage for enabling selective and individual retraction and extension of each electrode lead, whereby each of each lead is positionable from a retracted position wherein each lead is individually stored within a storage enclosure, to a manually extended position wherein each lead is dispensed from said storage enclosure such that each of said electrodes may be placed in contact with a patient for detecting signals relating to the patient's heart activity;

said storage enclosure having opposing first and second ends, each of said ends having a plurality of leads dispensed therefrom, whereby said storage enclosure may be disposed proximal to a patient's torso and leads may be dispensed toward the patient's upper torso from said first end, and additional leads may be dispensed toward the patient's lower torso and legs.

6. An assembly of sensors for use with an EKG machine according to claim 5, wherein said means for retractable storage includes:

a plurality of spools rotatably supported within said storage enclosure, each of said spools having a length of one of said electrode leads wound thereon.

7. An assembly of sensors for use with an EKG machine according to claim 6, wherein each of said spools is rotatably biased to a position wherein an electrode lead associated with a spool is substantially wound thereon within said storage enclosure and said electrode connected to said lead is substantially adjacent to said storage enclosure, whereby said leads are not subject to entanglement.

8. An assembly of sensors for use with an EKG machine according to claim 7, further including means for selective rotatable anchoring of each of said spools.

* * * * *